United States Patent [19]

Inui

[11] Patent Number: 4,704,494

[45] Date of Patent: Nov. 3, 1987

[54] CONVERSION PROCESS OF AROMATIC HYDROCARBON FROM LOW MOLECULAR PARAFFIN HYDROCARBON

[75] Inventor: Tomoyuki Inui, 35-21, Teradashodo, Joyo-shi, Kyoto 610-01, Japan

[73] Assignees: Showa Shell Sekiyu Kabushiki Kaisha, Tokyo; Tomoyuki Inui, Joyo, both of Japan

[21] Appl. No.: 22,561

[22] Filed: Mar. 4, 1987

Related U.S. Application Data

[63] Continuation of Ser. No. 913,604, Sep. 29, 1986, abandoned, which is a continuation of Ser. No. 762,956, Aug. 6, 1985, abandoned.

[30] Foreign Application Priority Data

Aug. 15, 1984 [JP] Japan ................... 59-169367

[51] Int. Cl.$^4$ .............................................. C07C 2/52
[52] U.S. Cl. ..................................... 585/417; 585/415
[58] Field of Search ............................. 585/415, 417

[56]      References Cited

U.S. PATENT DOCUMENTS

| 3,760,024 | 9/1973  | Cattanach . |         |
|-----------|---------|-------------|---------|
| 3,827,968 | 8/1974  | Givens .    |         |
| 4,120,910 | 10/1978 | Chu         | 585/417 |
| 4,157,293 | 6/1979  | Plank .     |         |
| 4,347,394 | 8/1982  | Detz et al. | 585/417 |
| 4,350,835 | 9/1982  | Chester et al. | 585/417 |
| 4,490,569 | 12/1984 | Chu et al.  | 585/415 |
| 4,497,970 | 2/1985  | Young       | 585/417 |

FOREIGN PATENT DOCUMENTS

| 0050021 | 4/1982 | European Pat. Off. | 585/415 |
| 0107875 | 5/1984 | European Pat. Off. | 585/417 |
| 0107876 | 5/1985 | European Pat. Off. | 585/417 |
| 0107877 | 5/1985 | European Pat. Off. | 585/417 |

OTHER PUBLICATIONS

Inui, Tomoyuki, Propane Conversion to Aromatic Hydrocarbons on Pt/H–ZSM-5 Catalysts.

Primary Examiner—Curtis R. Davis
Attorney, Agent, or Firm—Ladas & Parry

[57]          ABSTRACT

Low molecular paraffin hydrocarbons can be converted to aromatic hydrocarbons at high yields of 20–30% in the presence of a metallo-silicate catalyst (Si/Me) (wherein atomic ratio of Si/Me is 25–3200 and Me is Al, Ga, Ti, Zr, Ge, La, Mn, Cr, Sc, V, Fe, W, Mo or Ni) modified with 0.25–1.5% by weight of platinum or gallium or a gallium-silicate catalyst (atomic ratio of Si/Ga is 25–3200).

Since said catalyst is of high activity and reaction is carried out at low temperatures, reduction of selectivity of the catalyst caused by decomposition of aromatic hydrocarbons produced can be prevented.

11 Claims, 7 Drawing Figures

CONVERSION PROCESS OF AROMATIC HYDROCARBON FROM LOW MOLECULAR PARAFFIN HYDROCARBON

This is a continuation of co-pending application Ser. No. 913,604 filed on Sept. 29, 1986, which is a continuation of Ser. No. 762,956, filed Aug. 6, 1985.

BACKGROUND OF THE INVENTION

This invention relates to a process for conversion of a low molecular paraffin hydrocarbon to an aromatic hydrocarbon. More particularly, it relates to a process for conversion of a low molecular paraffin hydrocarbon of 5 or less carbon atoms such as ethane, propane, butane, pentane or a mixture thereof to an aromatic hydrocarbon.

Utilization of low molecular paraffin hydrocarbons contained in natural gas and light paraffin hydrocarbons produced from petroleum refining process is an important problem because these hydrocarbons are produced in large amounts.

Recently, there have been reported many processes to convert ethane to aromatic hydrocarbons with ion-exchanged H-ZSM-5 catalysts. For example, Mobil Oil Corporation has reported use of Cu-Zn/H-ZSH-5 catalysts in U.S. Pat. No. 4,120,910 (1978). Mobil Oil Corporation has further reported use of Ga/H-ZSM-5 catalysts in U.S. Pat. No. 4,350,835 (1982). Moreover, use of gallium-exchanged aliminosilicate has been reported in EPC Application No. 50,021.

However, according to the conventional processes, both the conversion of ethane and selecting to aromatic hydrocarbons are not high and improvement of catalysts and research of reaction characteristics have been required. For these reasons, researches have been made on novel catalysts for selective conversion of lower molecular paraffin hydrocarbons such as propane to liquid fuels or aromatic hydrocarbons.

The inventor has already made researches on process for producing aluminosilicate catalysts as disclosed in U. S. Pat. No. 4,400,328 (Aug. 23, 1983).

It has now been found that a catalyst comprising a combination of said metallo-silicate catalyst excellent in selectivity of catalyst form and a catalyst having dehydrogenation function and a gallium-silicate catalyst can convert low molecular paraffin hydrocarbons to aromatic hydrocarbons at a high conversion and a high selectivity.

SUMMARY OF THE INVENTION

It is, therefore, an object of this invention to provide a process for conversion of low molecular paraffin hydrocarbons to aromatic hydrocarbons at a high conversion and a high selectivity.

The above object is accomplished in accordance with this invention by carrying out treatment of a low molecular paraffin hydrocarbon in the presence of 0.25 to 1.5% by weight platinum- or gallium-modified metallo-silicate catalyst represented by the formula Si/Me (wherein atomic ratio of Si/Me is 25 to 3200 and Me means Al, Ga, Ti, Zr, Ge, La, Mn, Cr, Sc, V, Fe, W, Mo or Ni) or a gallium-silicate catalyst at a reaction temperature of 300° C. to 650° C.

DESCRIPTION OF THE INVENTION

Figure 1:
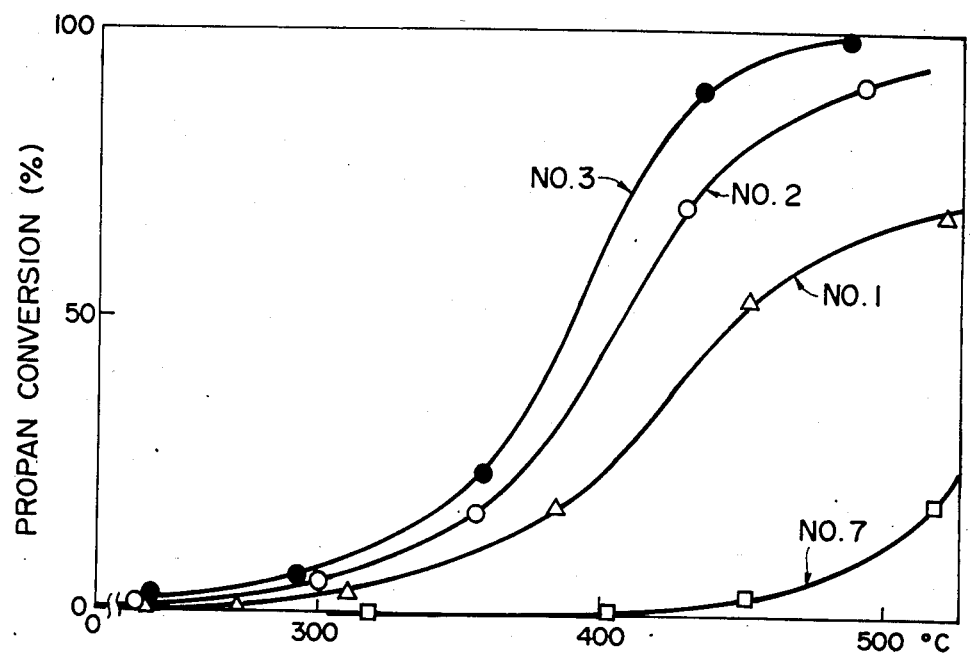
FIG. 1 is a graph which shows relation between propane conversion(%) and reaction temperature (°C.).

The conversion reaction of low molecular paraffin hydrocarbons to aromatic hydrocarbons includes dehydrogenation of the low molecular paraffin hydrocarbon (e.g. propane) to an olefinic hydrocarbon (e.g. propene) by action of dehydrogenation catalyst (e.g. Pt), and polymerization of the propene molecules at acidic point of metallo-silicate catalyst to produce high molecular olefin and the subsequently produce an aromatic hydrocarbon. Main reaction products are limited to methane, ethane and aromatic hydrocarbons, but production of the hydrocarbons of one and two carbon atoms must be prevented.

Preparation of Catalysts

The Pt or Ga/Metallo-silicate catalysts and Gasilicate catalysts used in this invention may be prepared as follows:

(1) Platinum-modified metallo-silicate catalysts

Pt is modified in a metallo-silicate catalyst (atomic ratio of Si/Me is 25 to 3200 and Me is Al, Ge, Ti, Zr, Ga, La, Mn, Cr, Sc, V, Fe, W, Mo or Ni) as a carrier by impregnation method or ion-exchanging method using an aqueous tetraamineplatinum salt [$Pt(NH_3)_4Cl_2$] solution of a given concentration.

The metallo-silicate catalyst is prepared in the following manner.

Solution A: An aqueous solution containing a metal salt (Me is a di- or tri-valent nitrate, sulfate or chloride and preferably nitrate of metal), a nitrogen-containing organic cation and an inorganic salt.

Solution B: An aqueous silicate solution.

Solution C: An aqueous solution of ion modifier (NaCl).

Each of solution A and solution B is added to solution C at a constant rate with restraining changes of concentrations of the components in each solution and therewith of gel mixture by adding the ion modifier to solution A and a nitrogen-containing organic cation, an inorganic acid and an alkali hydroxide to solution C (the first step). The resultant gel mixture is ground(the second step) and the gel mixture is heated from room temperature to 150° C.–190° C. at a constant rate and thereafter is further heated to 190° C.–220° C. at a constant rate or an exponential rate to perform hydrothermal synthesis reaction (the third step), thereby to obtain the desired metallo-silicate catalyst [Japanese Patent Unexamined Publication (Kokai) No. 12135/85].

Composition (mole ratio)

Si/Me: 25–3200
$OH^-/SiO_2$: 0.3–1.0
$H_2O/SiO_2$: 30–100
R/R+alkali metal: 0.05–0.15
$NaCl/H_2O$: 0.01–0.06

(In the above formulas, R is a quaternary alkylammonium cation, preferably quaternary propylammonium cation, the alkali metal is sodium or potassium and Me is Al, Ga, Ti, Zr, Ge, La, Mn, Cr, Sc, V, Fe, W, Mo or Ni.)

In the first step solution A and solution B are mixed with solution C by microfeeder at a constant rate so that the pH value becomes around 10. About 10 minutes is required for mixing of these solutions.

In the second step, the produced gel is separated from mother liquor by centrifugation, then is automatically ground in a mortar for 1 hour and therafter is combined with the mother liquor (the second step) and hydrothermal reaction of gel mixtures is performed under the following conditions.

The hydrothermal synthesis reaction of gel mixture is carried out by heating the mixture to 160° C. over the period of 90 minutes and then linearly to 210° C. over the period of 250 minutes with stirring in an autoclave (the third step). Then, the product is washed 8 times with about 60 ml of distilled water, dried and calcined in an air stream (flow velocity 100 ml/min) at 540° C. for 3.5 hours. After the calcination, the calcined product is subjected to ion-exchange treatment with a metal to be modified by dipping in twice in an aqueous $NH_4NO_3$ solution of 1 mol/l concentration at 80° C. for 1 hour with stirring. Thus treated product is washed three times with 60 ml of distilled water and calcined in air stream (100 ml/min) at 450° C. for 3.5 hours.

(2) Gallium-silicate catalyst

In the same manner as in preparation of the metallo-silicate catalyst (atomic ratio of Si/Me is 25–3200) used as a support for platinum-modified metallo-silicate catalyst (atomic ratio of Si/Me is 25–3200) as mentioned above, a gallium-silicate catalyst is prepared using, for example, $Ga_2(SO_4)_3.8H_2O$ which provides an atomic ratio of Si/Me of 25–3200.

Reaction Conditions

The catalysts used are metallo-silicate catalysts (atomic ratio of Si/Me is 25–3200) Me has the same meaning as defined above) modified with 0.25–1.5% by weight, preferably 0.5–1.0% by weight of Pt or Ga.

Metallo-silicate catalysts (Si/Me) used as a support are those in which Me is selected from Al, Ga, Ti, Zr, Ge, La, Mn, Cr, Sc, V, Fe, W, Mo and Ni and a mixture thereof.

Modification of Pt or Ga is carried out by ion-exchanging method or impregnating method.

For example, when Pt is modified by impregnating method, a metallo-silicate catalyst is impregnated with, for example, an aqueous solution of a water soluble teraamine-platinum salt $[Pt(NH_3)_4Cl_2]$, and then dried and the salt is heat-decomposed in air at 200°–400° C.

The gallium-silicate catalyst (Ga-silicate catalyst), is produced in the same manner as in the preparation of said metallo-silicate catalyst with use of, for example, $Ga_2(SO_4)_3.8H_2O$.

This invention can be further illustrated by the following examples, which are included merely for purposes of illustration and are not intended to limit the scope of the invention.

EXAMPLE 1

Pt-modified aluminosilicate catalyst (Pt/alumino-silicate catalyst) (atomic ratio of Si/Al is 40) and Ga-silicate catalyst (atomic ratio of Si/Ga is 40) prepared as mentioned above were tableted and then crushed to 10–20 meshes.

0.5 g of thus obtained catalyst was packed in a reaction tube of 6 mm in inner diameter and a mixed gas containing 20% by volume of propane and 80% by volume of nitrogen was subjected to reaction under atmospheric pressure and at SV (GHSV) of 2,000 $hr^{-1}$ and by elevating temperature at prescribed reaction temperature using a common atmospheric flow reaction apparatus.

Components of the conversion gas were analyzed by gas chromatography with an integrator.

Columns used were MS-5A, Silicon OV and VZ-10.

[A] Effect of method for preparation of catalyst on temperature dependence of propane conversion Relation between selectivity and temperature on aluminosilicate catalysts modified with various concentrations of platinum or gallium and Ga-silicate catalyst was studied and compared with aluminosilicate catalyst. The results are shown in Table 1.

Relation between propane conversion and reaction temperature (200°–500° C.) in case of using Pt/aluminosilicate catalysts, Ga/aluminosilicate catalyst, Ga-silicate catalyst and H-ZSM-5 catalyst as shown in Table 1 is shown in FIG. 1.

Reaction conditions were feed gas comprising 20% by volume of $C_3H_8$ and 80% by volume of $N_2$ and SV is 2000 $hr^{-1}$.

TABLE 1

| | Catalyst | | | | | | |
|---|---|---|---|---|---|---|---|
| | No. 1<br>0.5 wt % Pt/<br>alumino-<br>silicate<br>Impregnation<br>method<br>(Si/Al = 40) | No. 2<br>0.5 wt % Pt/<br>alumino-<br>silicate<br>Ion-exchange<br>method<br>(Si/Al = 40) | No. 3<br>1.0 wt % Pt/<br>alumino-<br>silicate<br>Ion-exchange<br>method<br>(Si/Al = 40) | No. 4<br>1.0 wt % Pt/<br>alumino-<br>silicate<br>Ion-exchange<br>method<br>(Si/Al = 3200) | No. 5<br>1.0 wt % Ga/<br>alumino-<br>silicate<br>Ion-exchange<br>method<br>(Si/Al = 3200) | No. 6<br>1.0 wt % Ga<br>-silicate<br>(Si/Ga = 40) | No. 7<br>Alumino-<br>silicate<br>(H-ZSM-5)<br>(Si/Al = 40) |
| $C_3H_8$<br>conversion<br>(%) | 67.8 | 92.0 | 99.8 | 96.6 | 95.7 | 82.4 | 11.5 |
| Selectivity<br>(C-wt %) | | | | | | | |
| $CH_4$ | 6.1 | 13.8 | 41.3 | 23.7 | 20.5 | 8.9 | 25.5 |

TABLE 1-continued

| | Catalyst | | | | | | |
|---|---|---|---|---|---|---|---|
| | No. 1 0.5 wt % Pt/ alumino-silicate Impregnation method (Si/Al = 40) | No. 2 0.5 wt % Pt/ alumino-silicate Ion-exchange method (Si/Al = 40) | No. 3 1.0 wt % Pt/ alumino-silicate Ion-exchange method (Si/Al = 40) | No. 4 1.0 wt % Pt/ alumino-silicate Ion-exchange method (Si/Al = 3200) | No. 5 1.0 wt % Ga/ alumino-silicate Ion-exchange method (Si/Al = 3200) | No. 6 1.0 wt % Ga -silicate (Si/Ga = 40) | No. 7 Alumino-silicate (H-ZSM-5) (Si/Al = 40) |
| $C_2H_6$ | 57.0 | 56.2 | 26.7 | 44.7 | 37.7 | 55.7 | 8.1 |
| $C_2H_4$ | 2.4 | 1.8 | 2.2 | 4.0 | 8.5 | 2.1 | 30.1 |
| $C_3H_6$ | 10.0 | 3.1 | 0.3 | 2.1 | 1.5 | 8.5 | 21.1 |
| $C_4$ + aromatic | 3.0 | 0.6 | 0.4 | 0.4 | 4.3 | 2.3 | 9.5 |
| Aromatics | 21.5 | 24.5 | 29.1 | 25.6 | 27.5 | 27.5 | 5.2 |

It is recognized from Table 1 and FIG. 1 that the reactions began at a reaction temperature of about 300° C. with both the catalysts prepared by impregnation method and ion-exdhange method and Ga-silicate catalyst. Furthermore, the catalysts prepared by impregnation method provided a conversion of 70% at maximum at 500° C. while those by ion-exchange method attained a conversion of more than 90%. This is considered to be attributable to the fact that Pt and Ga modified by ion-exchange method diffuse into micro-structure of the silicate catalyst more effectively than those modified by impregnation method.

With reference to Pt/aluminosilicate catalysts (atomic ratio of si/Al is 25–3200), when Pt content is less than 0.25% by weight the propane conversion is low and when more than 1.5% by weight the predominant reaction is a decomposition reaction and selectivity to aromatics is low. Preferred range is 0.5–1.0% by weight.

With reference to Ga-modified aluminosilicate (Ga/aluminosilicate) catalysts (atomic ratio of Si/Al is 25–3200) and Ga-silicate catalyst, Ga content is similar to the Pt content.

[B] Temperature dependence of amounts of hydrocarbons in the conversion gas 0.5% by weight Pt/aluminosilicate catalyst (atomic ratio of Si/Al is 40) prepared by impregnation method was used.

Reaction conditions were SV of 2000 hr$^{-1}$ and reaction temperature 300°–650° C. with feed gas of $C_3H_8$ 20% and $N_2$ 80%.

Figure 2:
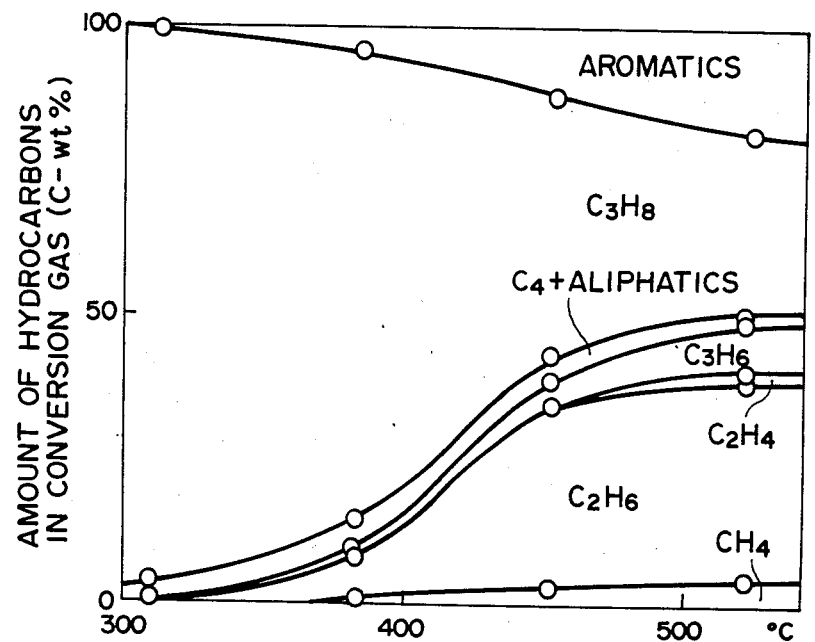
FIG. 2 is a graph which shows relation between reaction temperature (°C.) and amount of hydrocarbons in conversion gas (C-wt %) when a 0.5% by weight Pt/alumino-silicate catalyst prepared by impregnation (No. 1 was used.

Amounts of aromatic hydrocarbons, paraffin hydrocarbons of $C_4$ and higher, $C_3H_6$, $C_2H_4$, $C_2H_6$, $CH_4$ and $C_3H_8$ were determined and the results are shown in FIG. 2.

Figure 3:
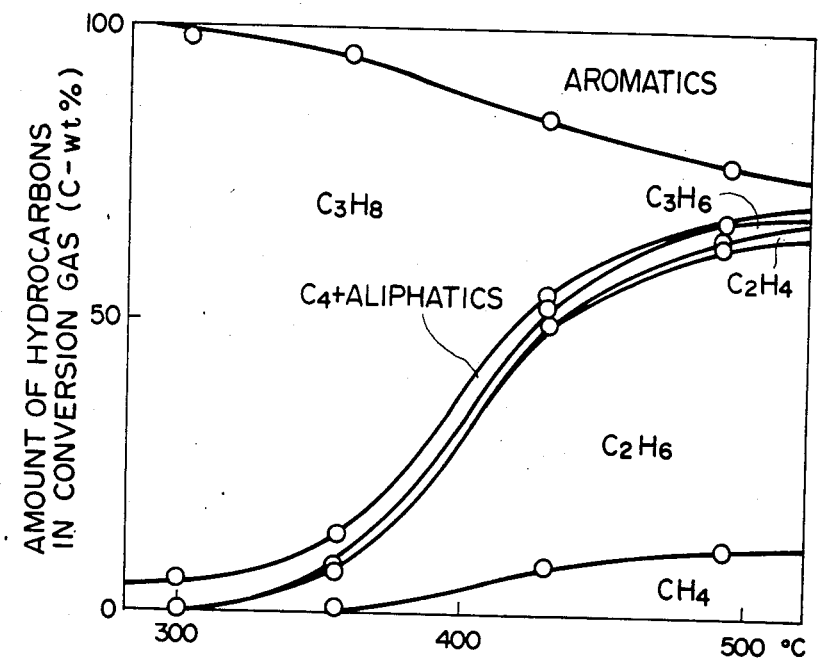
FIG. 3 is a graph which shows relation between reaction temperature (°C.) and amount of hydrocarbons in conversion gas (C-wt %) when a 0.5% by weight Pt/alumino-silicate catalyst prepared by ion-exchanging method (No. 2) was used.

The same test was conducted using 0.5% by weight Pt/aluminosilicate catalyst (atomic ratio of Si/Al is 40) prepared by ion-exchange method and the results are shown in FIG. 3.

Figure 4:
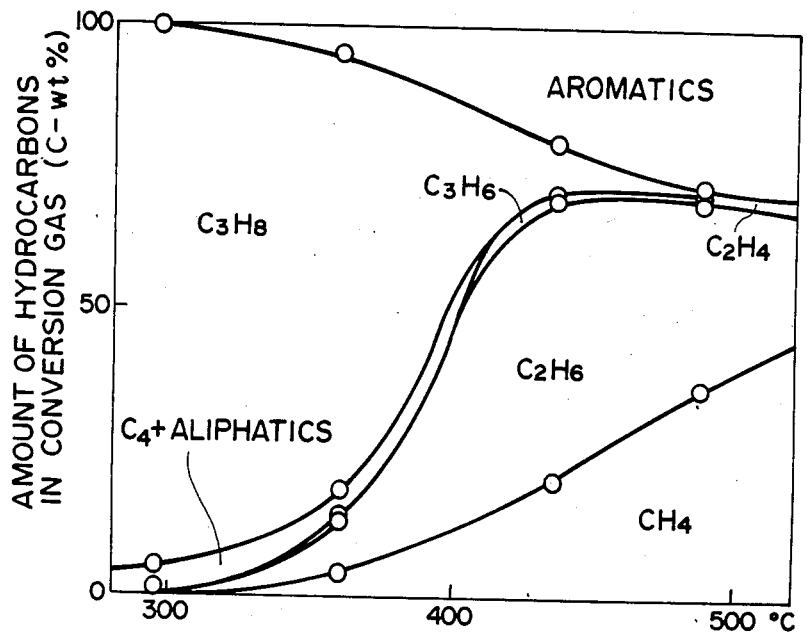
FIG. 4 is a graph which shows relation between reaction temperature (°C.) and amount of hydrocarbons in conversion gas (C-wt %) when a 1.0% by weight Pt/alumino-silicate catalyst prepared by ion-exchanging method (No. 3) was used.

The same test was further carried out using 1.0% by weight Pt/aluminosilicate catalyst (atomic ratio of Si/Al is 40) prepared by ion-exchange method and the results are shown in FIG. 4.

The reaction conditions were the same as above.

It was recognized from FIGS. 2, 3 and 4 that the catalysts prepared by ion-exchange method afforded higher propane conversion, and higher $C_1$–$C_2$ hydrocarbon contents and aromatic hydrocarbon contents in the conversion gas than the catalysts prepared by impregnation method at the same reaction temperature.

With reference to the reaction temperature dependence both the catalysts prepared by impregnation method and ion-exchange method exhibited the similar trend. That is, with increase in reaction temperature, contents of $C_1$–$C_2$ hydrocarbons and aromatic hydrocarbons in the conversion gas increased and at a temperature higher than 400° C. most of the hydrocarbons of 4 or more carbon atoms were aromatic hydrocarbons.

It seems that propane in the feed gas was converted to propene by dehydrogenation function of platinum component of the catalyst and the propene is to be polymerized to polymeric olefins, but because of the high reaction temperature the polymeric olefins were all converted to $C_1$–$C_2$ hydrocarbons and aromatic hydrocarbons.

As explained above, since the modified metallic Pt and Ga having dehydrogenation function are uniformly contained in microstructure of the metallo-silicate catalysts and the conversion reaction of paraffin hydrocarbons to aromatic hydrocarbons is effected at low temperatures due to high activity of the catalysts, decrease of selectivity caused by decomposition of the aromatic hydrocarbons can be prevented to result in increase of yield of aromatic hydrocarbons.

[C] Effect of conversion temperature upon product selectivity in $C_2$–$C_5$ paraffin hydrocarbons Relation between conversion of $C_2$–$C_5$ paraffin hydrocarbon and temperature on 1.0 wt % Pt-modified aluminosilicate catalyst was studied. The results are shown in FIG. 5.

Figure 5:
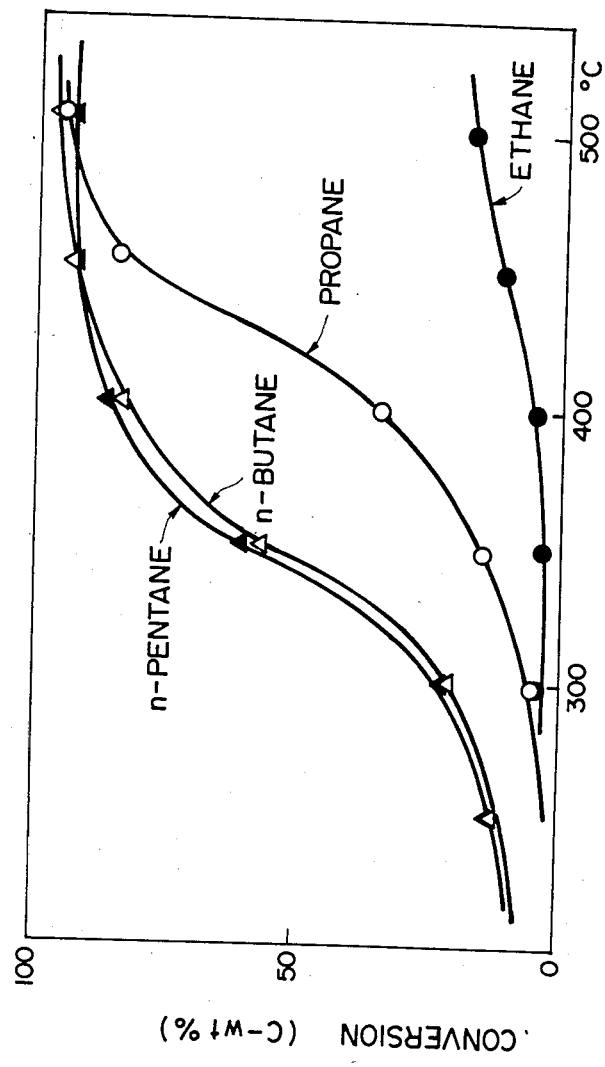
FIG. 5 is a graph which shows relation between propane conversion (C-wt %) and temperature (°C.).

FIG. 5 shows that conversions of n-butane and n-pentane are relatively higher than that of propane under a relatively low temperature range of 300°–450° C., and that conversions of n-butane, n-pentane and propane at the temperature of 500° C. reaches about 95%. Conversion of ethane is only as small as about 18%.

The product selectivity of $C_2$–$C_5$ paraffin hydrocarbons at about 500° C. is shown in Table 2.

Product selectivity of aromatic hydrocarbon becomes higher as carbon numbers in $C_3$–$C_5$ hydrocarbon decrease, and the highest in case of propane.

TABLE 2

| | Product selectivity of each feed gas | | | |
|---|---|---|---|---|
| | Feed gas | | | |
| Selectivity (C-wt %) | $C_2H_6$ | $C_3H_8$ | n-$C_4H_{10}$ | n-$C_5H_{12}$ |
| | Conversion (%) | | | |
| | 17.91 | 96.42 | 96.91 | 92.93 |
| $C_1$ | 33.61 | 23.55 | 8.93 | 2.68 |
| $C_2$ | feed | 41.82 | 40.21 | 35.85 |
| $C_2$= | 35.23 | 3.32 | 1.96 | 2.58 |
| $C_3$ | 7.09 | feed | 13.18 | 19.81 |
| $C_3$= | 7.09 | 2.13 | 5.37 | 7.09 |
| iso-$C_4$ | tr. | tr. | 1.79 | 3.68 |
| n-$C_4$ | 0.11 | tr. | feed | 2.85 |
| $C_4$= | 0.17 | tr. | 1.72 | 3.32 |

TABLE 2-continued

| Selectivity (C-wt %) | Product selectivity of each feed gas | | | |
|---|---|---|---|---|
| | Feed gas | | | |
| | $C_2H_6$ | $C_3H_8$ | $n\text{-}C_4H_{10}$ | $n\text{-}C_5H_{12}$ |
| | Conversion (%) | | | |
| | 17.91 | 96.42 | 96.91 | 92.93 |
| iso-$C_5$ | tr. | tr. | 0.14 | 0.98 |
| n-$C_5$ | 0.28 | 0.03 | 0.10 | feed |
| $C_5=$ | 0.06 | 0.03 | 0.10 | 0.16 |
| $C_6$+Aliphatics | tr. | 0.02 | 0.17 | 0.75 |
| Aromatics | 16.36 | 29.10 | 26.33 | 20.25 |

Cat. 1.0 wt % Pt/H-ZSM-5 (ion-exchange)
Feed paraffin (vol %) 20%, $N_2$ 80%, SV = 2000 hr$^{-1}$
Reaction Temp. 500° C.

EXAMPLES 2-3

Example 1 was repeated except a Ga-silicate catalyst and a Pt-modified Ga-silicate catalyst were employed, respectively, in place of the Pt-modified aluminosilicate catalyst.

Table 3 shows results when Ga-silicate catalysts in which amounts of Ga contained are varied were used and reaction was conducted at 600° C. Propane conversion and product selectivity remarkably increase as amounts of Ga contained in the catalyst are greater. Ga-silicate catalyst is superior to the Ga-ionexchanged ZSM-5 catalyst with respect to product selectivity. Ga-silicate catalyst is very active to produce aromatic hydrocarbons from propane.

TABLE 3

| Selectivity (C-wt %) | Product selectivity for each Si/Ga catalyst and Ga/ZSM-5 catalyst | | | |
|---|---|---|---|---|
| | Catalyst | | | |
| | Si/ Ga = 40 | Si/ Ga = 25 | Si/ Ga = 21 | 0.5 wt % Ga/ H-ZSM-5 (ionexchange method) |
| | $C_3H_8$ conv. (%) | | | |
| | 25.9 | 62.4 | 81.6 | 52.4 |
| $CH_4$ | 14.6 | 12.1 | 10.4 | 20.0 |
| $C_2H_6$ | 5.4 | 8.5 | 7.5 | 6.5 |
| $C_2H_4$ | 19.5 | 9.1 | 7.6 | 18.7 |
| $C_3H_6$ | 18.3 | 8.0 | 6.4 | 12.1 |
| $C_4$+Aliphatics | 4.3 | 1.1 | 0.7 | 2.7 |
| Aromatics | 37.9 | 61.2 | 67.4 | 40.0 |

Feed gas: $C_3H_8$ 20%, $N_2$ 80%, SV = 2000 hr$^{-1}$, Reaction Temp. 600° C.

Figure 6:
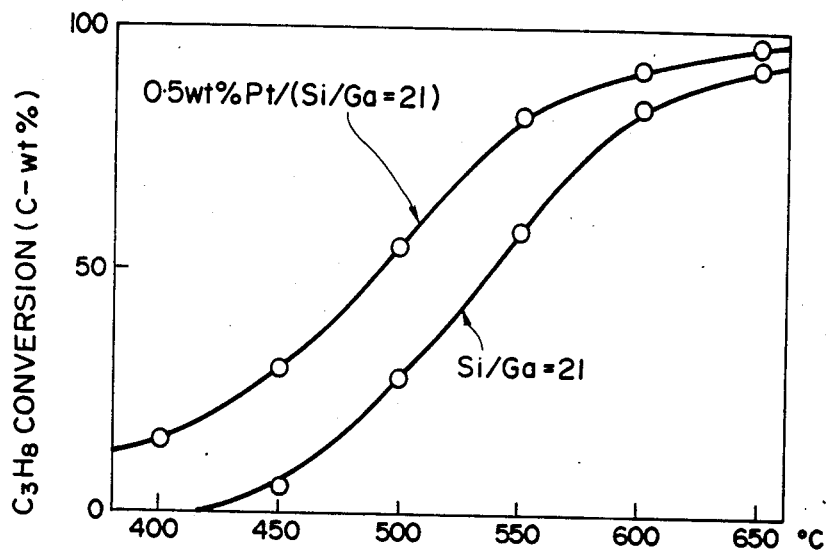
FIG. 6 is a graph which shows propane conversion in comparison of Pt-modified Ga-silicate catalyst with Ga-silicate catalyst at the temperature of 400°-650° C.

FIG. 6 shows influences of modification of Pt in the propane conversion reaction when 0.5% Pt-modified Ga-silicate catalyst was employed. Modification of the Ga-silicate catalyst with Pt was effected by the ion exchange method using Pt(NH$_4$)$_4$Cl$_2$. Propane conversion moved to the lower temperature region, in comparison with the Ga-silicate catalyst.

Figure 7:
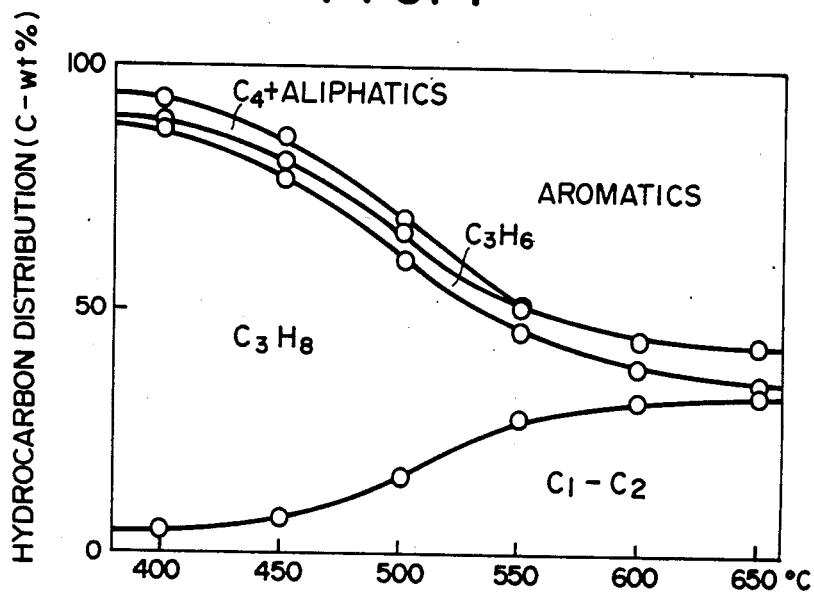
FIG. 7 is a graph which shows distribution of hydrocarbons in effluent gas of the propane conversion reaction at the temperature of 400°-650° C.

FIG. 7 shows distribution of hydrocarbons in effluent gas when propane conversion was effected using a 0.5 wt % Pt-modified Ga-silicate catalyst. Product selectivity and yield were 59.1% and 40.4%, respectively, at the optimum temperature of 550° C. for the catalyst. Product selectivity and yield are 24.5% and 22.5%, respectively, at the optimum temperature of 500° C. for the 0.5 wt % Pt-modified ZSM-5 catalyst [T. Inui, F. Okazumi: J. Cat., 90, 366 (1984)]. Selectivity and yield when the present Pt-modified Ga-silicate catalyst was used were about twice as much as when the conventional catalyst was used.

What is claimed is:

1. A process for conversion of low molecular paraffin hydrocarbon to aromatic hydrocarbon which comprises bringing the low molecular paraffin hydrocarbons into contact with a metallo-silicate catalyst (Si/Me) wherein the atomic ratio of Si/Me is 25-3200, and Me is one selected from the group consisting of Al, Ga, Ti, Zr, Ge, La, Mn, Cr, Sc, V, Fe, W, Mo and Ni, which is impregnated or ion-exchanged with 0.25-1.5% by weight of platinum or gallium, based on the catalyst, or a gallium-silicate catalyst wherein the atomic ratio of Si/Ga is 20-3200, said catalyst being prepared by the following steps; a first step of preparing solutions of (A), (B) and (C), said (A) being an aqueous solution containing (a) a quaternary lower alkylammonium cation R, (b) an alkaline metal of sodium or potassium, and (c) an aqueous solution of a water soluble salt of a metal Me selected from the group consisting of Al, Ga, Ti, Zr, Ge, La, Mn, Cr, Sc, V, Fe, W, Mo and Ni; (B) an aqueous silicate solution, and (C) an aqueous solution of an ion modifier, and adding the solution (A) and solution (B) to the solution (C) at a constant speed until a gelly mixture having a pH of around 10; a second step of grinding the resulting gel mixture; a third step of heating the gel mixture to a temperature of 150°-190° C. at a constant speed followed by heating to 190°-200° C. at a constant speed or an exponential speed to obtain a precourser synthetic metallosilicate having the following chemical composition in molar ratio:

Si/Me: 25-3200
OH$^-$SiO$_2$: 0.3-1.0
H$_2$O/SiO$_2$: 30-100
R/R+alkalimetal: 0.05-0.15
NaCl/H$_2$O: 0.01-0.06 wherein R is a quaternary alkylammonium cation, the alkali metal is sodium or potassium and Me is Al, Ga, Ti, Zr, Ge, La, Mn, Cr, Sc, V, Fe, W, Mo or Ni and fourth step of calcining the precourser.

2. A process as claimed in claim 1 wherein the quaternary alkylammonium cation is quaternary propylammonium cation.

3. A process as claimed in claim 1 wherein the ion modifier is sodium chloride.

4. A process as claimed in claim 1 wherein the temperature of contacting said low molecular paraffin hydrocarbons with said metallo-silicate catalyst is in the range of 350°-650° C.

5. A process as claimed in claim 4 wherein said temperature is in the range of 350°-500° C.

6. A process as in claim 1 wherein said fourth step of calcination comprises heating to about 540° C. for about 3.5 hours.

7. A process as in claim 6 wherein after the first calcination the resulting product is washed and calcinated in air at about 450° C. for about 3.5 hours.

8. A process as in claim 1 wherein the ratio of Si/Ga is about 20.

9. A process as in claim 1 wherein the ratio of Si/Ga is in the range of about 20-35.

10. A process as in claim 1 wherein the ratio of Si/Ga is in the range of 21-35.

11. A process as in claim 1 wherein the metallo-silicate catalyst is modified with 0.5-1.0% by weight of platinum or gallium.

* * * * *